(12) United States Patent
Phillips

(10) Patent No.: US 6,392,420 B1
(45) Date of Patent: May 21, 2002

(54) CAN COATING TESTER

(75) Inventor: Roger Phillips, Oxfordshire (GB)

(73) Assignee: Crown Cork & Seal Technologies Corporation, Alsip, IL (US)

( * ) Notice: Subject to any disclaimer, the term of this patent is extended or adjusted under 35 U.S.C. 154(b) by 0 days.

(21) Appl. No.: 09/622,339

(22) PCT Filed: Feb. 3, 1999

(86) PCT No.: PCT/GB99/00366

§ 371 Date: Aug. 16, 2000

§ 102(e) Date: Aug. 16, 2000

(87) PCT Pub. No.: WO99/44047

PCT Pub. Date: Sep. 2, 1999

(30) Foreign Application Priority Data

Feb. 24, 1998 (GB) .............................................. 9803678

(51) Int. Cl.[7] .............................................. G01R 31/12
(52) U.S. Cl. ..................................................... 324/557
(58) Field of Search ................................. 324/557, 690, 324/446; 73/150 R

(56) References Cited

U.S. PATENT DOCUMENTS

| | | | | |
|---|---|---|---|---|
| 3,417,327 A | * | 12/1968 | Breidenback | 324/557 |
| 3,719,884 A | * | 3/1973 | Laroche | 324/557 |
| 4,112,353 A | * | 9/1978 | Thompson | 324/557 |
| 4,206,407 A | * | 6/1980 | Bender | 324/446 |
| 4,894,251 A | | 1/1990 | Sieverin | |
| 5,373,734 A | * | 12/1994 | Shih et al. | 73/150 R |
| 5,698,085 A | * | 12/1997 | Yu | 204/434 |

FOREIGN PATENT DOCUMENTS

| | | |
|---|---|---|
| EP | 0723148 A2 | 1/1996 |
| GB | 2195771 A | 8/1987 |

* cited by examiner

*Primary Examiner*—Safet Metjahic
*Assistant Examiner*—Vincent Q. Nguyen
(74) *Attorney, Agent, or Firm*—Diller, Ramik & Wight

(57) ABSTRACT

The integrity and quality of the internal or inside coating of a container, such as a can, is measured by attaching an electric terminal to the can, inserting an electrode into the can, applying an electric signal to either the electric terminal or the electrode, and measuring the current flowing between the terminal and the electrode as an electrolyte is being added to the can. By measuring the electric signal as the level of electrolyte is being varied, an indication can be achieved of the quality and integrity of the coating at various parts of the can.

13 Claims, 1 Drawing Sheet

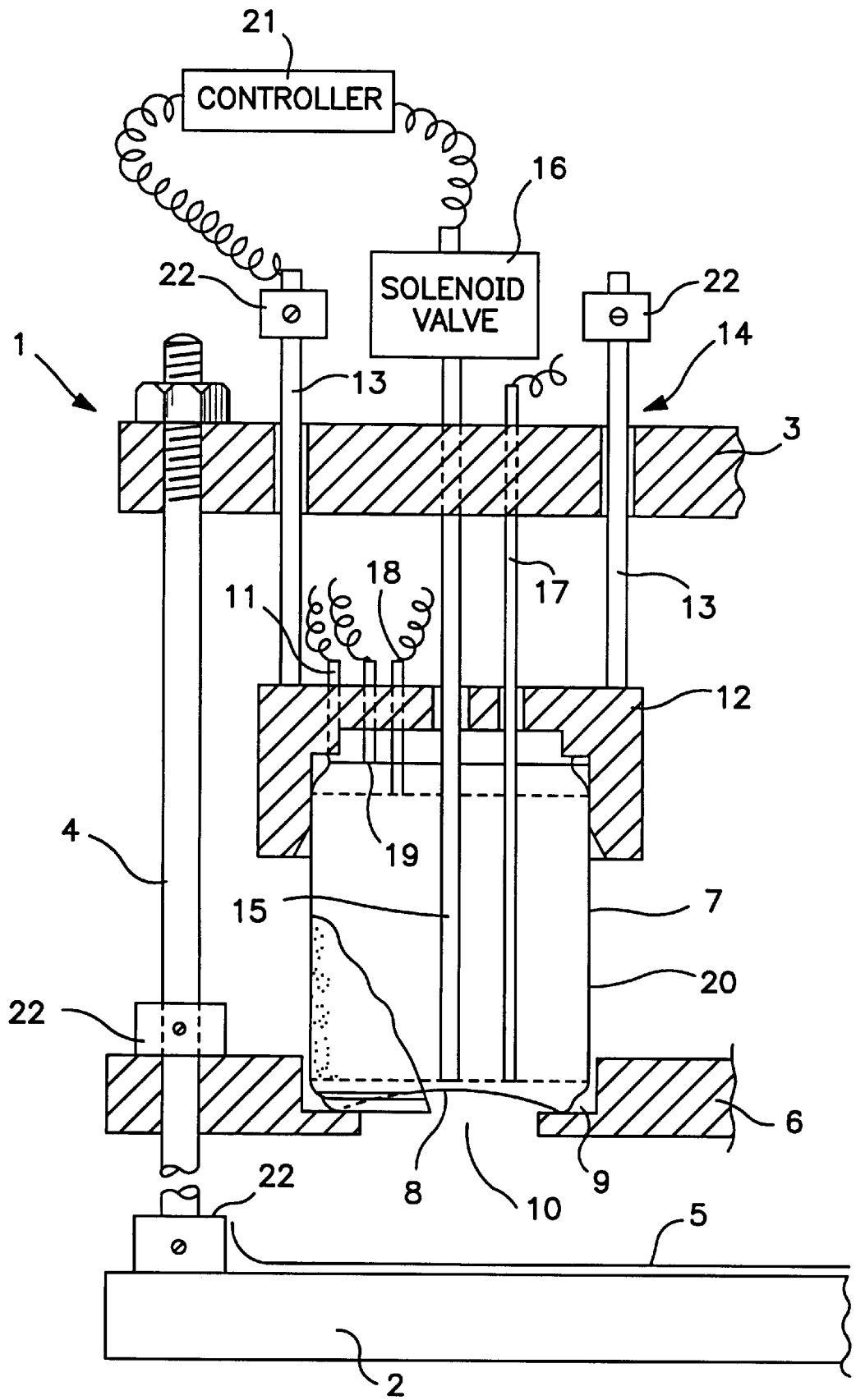

CAN COATING TESTER

BACKGROUND OF THE INVENTION

This invention relates to the testing of containers such as cans, and in particular to the testing of the integrity and quality of the internal coating of the can.

A well established method of measuring internal coating integrity is the "enamel rater," one example of which is in U.S. Pat. No. 4,206,407. The can to be tested is filled with electrolyte and a DC signal is applied to the can. By measuring the current flow, an indication of the metal exposure can be obtained.

It has also been proposed to measure the thickness of can coatings by pressing a conductive rubber probe against the coating surface, to form a capacitor, and measuring the value of the capacitance to give an indication of the coating thickness. In one arrangement the can is filled with electrolyte rather than using a conductive rubber probe. These testing systems suffer from various disadvantages, the rubber probe method can only give "spot" readings from individual areas of the inside can surface, and therefore requires a large number of repeated measurements to give any sort of overall picture of the can coating. The electrolyte gives a general overall indication of the can coating thickness, but it cannot give any sort of indication of distribution of coating material on different parts of the can. The present invention provides an improvement to these types of measuring systems.

SUMMARY OF THE INVENTION

Accordingly there is provided a method of measuring the quality of the coating on the inside of a can which comprises the steps of:
 i. attaching at least one electric terminal to the can;
 ii. inserting an elongate electrode into the can;
 iii. applying an electrical signal to either the electrode or electric terminal;
 iv. adding an electrolyte to the can; and
 v. measuring the current flowing between the electrode and the electric terminal as the level of the electrolyte is being varied in a controlled manner in order to give an indication of the quality of the coating at various parts of the can.

By measuring the current flowing as the level of the electrolyte in the can is being varied, readings representing the coating quality at different parts of the can may be generated. For example, a reading may be generated which represents the coating quality of the base of the can, at various positions up the cylindrical sidewall of the can, or even possibly at the necked-in portion of the can. Level detectors may be employed to associate the timing of the electrical readings with the progression of the electrolyte up or down the can as it is filled with or emptied of fluid. Preferably, the current is measured as the electrolyte is being added to the can.

The method preferably includes the step of applying an ac signal to either the electrode or the electric terminals, and conveniently of measuring the capacitance of the can. As previously mentioned, the capacitance reading may be used to give an indication of the coating thickness, and by measuring the capacitance as the electrolyte level is being varied, the can coating thickness at various positions within the can may be established. This may help to determine, for example, the distribution of coating material within the can as between the sidewall and the base, or between different areas of the sidewall itself.

Conveniently, the method additionally or alternatively includes the step of measuring the phase relationship between the AC voltage signal applied between the electrode and the electric terminal, and the current flowing between the electrode and the electric terminal. This phase shift signal will depend on both the resistance and capacitance values of the can circuit. Ideally, the can circuit will comprise a small resistance derived from the electrolyte in series with a capacitance derived from the dielectric properties of the can coating. Ideally, the phase relationship should vary in a consistent manner as the level of electrolyte in the can is varied. However, if there is a gross disconformity in the can coating, this will result in metal exposure, and a conductive path through the coating which will significantly alter both the can circuit and the phase relationship. In this way, not only the presence but also the approximate location of any such disconformities can be detected. Similarly, any problems with the electrical connection between the electric terminal and the can will affect the resistance of the circuit and, hence, the phase shift signal.

The current flowing is preferably converted to an analogue AC voltage by an appropriate electronic circuit, which itself will introduce a phase shift. A convenient method of measuring a parameter which will be indicative of the integrity of the can coating is to apply the AC signal to a fixed circuit comprising a resistor and capacitor in series, and converting the current to an analog AC voltage using an electronic circuit identical to that used for conversion of the can current. The phase difference between the two analogue voltages can then be measured, and it is the way in which this parameter varies as the electrolyte level in the can is varied which indicates whether or not the can coating is of acceptable integrity, and if not, the magnitude and position of defects.

Preferably the method includes the step of interpreting the measured current in terms of the dry film weight of the can coating. To do this it is necessary to have a calibration factor for the particular coating being used, which calibration factor is used to relate the capacitance value to the dry film weight of the coating on the can. To determine this calibration factor a gravimetric measurement of the cans is made (i.e. weighing the cans before and after the coating has been applied), and the film weight measured is compared to the capacitance values obtained. In this way the capacitance values can be directly interpreted into dry film weight readings for that particular coating material.

The invention further resides in apparatus for measuring the quality of a coating on the inside of a can, the apparatus comprising
 i. at least one electric terminal adapted to be attached to the can;
 ii. an elongate electrode adapted to be inserted into the can;
 iii. a power supply for applying an electrical signal to either the electrode or the electric terminal;
 iv. means for adding an electrolyte to the can and varying the level of the electrolyte in the can at a controlled rate; and
 v. means for measuring the current flowing between the electrode and the electric terminal as the level of the electrolyte is being varied, in order to give an indication of the quality of the coating at various parts of the can.

BRIEF DESCRIPTION OF THE DRAWING

The invention will now be further described by way of example only, with reference to the accompanying drawing, which is a schematic sectional view of apparatus according to the present invention.

DESCRIPTION OF THE PREFERRED EMBODIMENTS

The apparatus includes a frame 1 comprising a bottom plate 2 and an upper plate 3 spaced apart by parts or posts 4. The bottom plate 2 carries a drip tray 5. Slidably mounted on the posts 4, between the bottom plate 2 and the upper plate 3, is a can holding plate 6 on which is supported a can 7 with a base 8 being received in a recess 9 in the can holding plate. The plate 6 has a central hole 10 in order to allow any drips to pass through (when the can is not present) to be caught by the drip tray.

The top of the can 7 is supported by an insulating holder 12 which depends from two supports 13 passing through the upper plate 3 by means of bushes 14. The holder 12 houses electric terminal assemblies or terminals making an electrical connection with the top of the can 7. A tubular electrode 15 passes through a hole in the upper plate 3 and extends into the can 7, its lower end lying adjacent the inside surface of the base 8 of the can 7.

The electrode 15 is connected to a solenoid valve 16 which controls the flow of electrolyte (not shown) which can be pumped through the electrode 15 into the can. Level detectors 17, 18, and 19 detect the level of the electrolyte within the can, the detector 17 measuring when the electrolyte reaches the level of the bottom of the sidewall 20 of the can. Detector 18 measures when the electrolyte reaches the level of the top of the sidewall 20, and detector 19 measures when the can is completely full of electrolyte. The terminal assemblies 11 and electrode 15 are each connected to a controller 21 which includes an AC sinewave generator.

In use, a can 7 is placed on the support 6, and the support is raised so that the top of the can is received in the holder 12. Stops 22 are used to govern the movement of the various components. When the can is in position, the controller 21 applies a 2.5 kHz sinewave at an RMS voltage of 300 mV to the electrode 15, and switches the solenoid valve 16 to allow electrolyte to flow into the can at a controlled rate, under the action of a pump (not shown). The controller 21 measures the current flowing between the terminals 11 and the electrode 15 through the electrolyte 11 and the can as the can is filling with electrolyte. Signals from the level detectors 17, 18 and 19 are also sent to the controller 21, so that it can determine the level of electrolyte within the can. When a signal is received from the level detector 19, the solenoid valve is closed to stop the supply of electrolyte, and the cycle is complete.

The controller 21 calculates the capacitance of the circuit between the terminals 11 and the electrode 15, which can be used to calculate the dry film weight of the coating on the inside of the can, provided a calibration factor has been determined for the coating concerned. The calibration factor is calculated by comparing the capacitance readings with the dry film weight measured by the well known gravimetric method, which is essentially weighing the can before and after the coating has been applied.

As the readings are taken as the can is filling with electrolyte, the film weight of the coating applied to various parts of the can may be determined. Table 1 shows the mean film weights calculated for two batches of 12 cans taken from two different spray machines on a can making line. Readings for the base, neck, and five areas along the cylindrical sidewall are given. In this way the distribution of coating within the can may be seen, and also how the application of coating from one can making line differs from another. The relatively high standard deviation for the base readings of the cans from machine 2, may be explained by certain coating deficiencies, which were confirmed by further investigation of these particular cans.

The controller 21 also measures the phase shift between the AC voltage signal as applied to the electrode 15 and the current measured flowing between the electrode and the terminals. The controller 21 applies the AC signal to a fixed resistor/capacitor circuit within the controller, and measures the difference between the phase shift signals of these two circuits. The phase shift signal can be used to check for proper electrical connection to the can 7, and also for gross disconformities in the coating, which could influence the calculation of film weight.

Table 2 shows similar measurements of batches of cans from 6 spray machines on a single can line. For the great majority of the cans, the phase shift signal was in a narrow range of 100 to 120. However, for a few cans, mainly from machine 4 and including 2 from machine 6, the cans gave abnormally high phase shift signals in excess of 200, indicating suspect film weight readings. Accordingly these readings were not included in those given in Table 2. Further analysis of the cans showed that there was metal exposure in the base area of the cans, possibly caused by the fact that the film weight readings were generally lower for lines 4 and 6.

It can therefore be seen that the testing equipment of the present invention is capable of measuring the distribution of coatings within a can, and comparing the performance of different coating spray equipment. It is also capable of identifying irregularities which would otherwise influence the film weight readings, so that these can be further investigated and/or disregarded.

TABLE 1

|  | MACHINE 1 | MACHINE 2 |
|---|---|---|
| Base | 8.0(sd 0.24) | 6.1(sd 0.93) |
| SW1 | 5.9(sd 0.19) | 5.6(sd 0.16) |
| SW2 | 5.8(sd 0.08) | 6.5(sd 0.18) |
| SW3 | 5.8(sd 0.06) | 7.4(sd 0.16) |
| SW4 | 4.9(sd 0.06) | 7.7(sd 0.11) |
| SW5 | 4.6(sd 0.07) | 7.5(sd 0.17) |
| Neck | 3.8(sd 0.03) | 4.3(sd 0.05) |
| Total(mg) | 152.0(sd 1.20) | 164.0(sd 2.20) |

TABLE 2

| | MACHINE NUMBER | | | | | |
|---|---|---|---|---|---|---|
| | 1 | 2 | 3 | 4 | 5 | 6 |
| No. in batch | 25 | 9 | 30 | 19 | 32 | 25 |
| base | 9.0(0.39) | 8.6(0.26) | 9.4(0.26) | 7.7(0.24) | 9.5(0.31) | 7.7(0.50) |
| SW1 | 6.2(0.20) | 5.1(0.13) | 5.6(0.22) | 6.0(0.17) | 6.3(0.15) | 5.8(0.23) |

TABLE 2-continued

| | MACHINE NUMBER | | | | | |
|---|---|---|---|---|---|---|
| No. in batch | 1<br>25 | 2<br>9 | 3<br>30 | 4<br>19 | 5<br>32 | 6<br>25 |
| SW2 | 6.7(0.27) | 5.8(0.23) | 5.7(0.17) | 6 7(0.18) | 6.4(0.16) | 6.4(0.30) |
| SW3 | 6.6(0.32) | 6.5(0.22) | 5.8(0.13) | 6.4(0.14) | 6.1(0.12) | 6.8(0.18) |
| SW4 | 6.1(0.28) | 6.0(0.14) | 5.8(0.13) | 5.6(0.15) | 5.6(0.12) | 6.4(0.15) |
| SW5 | 5.7(0.24) | 5.1(0.19) | 6.0(0.16) | 5.1(0.10) | 5.3(0.10) | 5.7(0.16) |
| neck | 4.4(0.13) | 3.3(0.16) | 4.4(0.11) | 4.3(0.05) | 4.3(0.07) | 4.3(0.11) |
| Total mg | 178(3.4) | 162(2.0) | 173(2.6) | 164(2.2) | 175(2.2) | 168(2.9) |

What is claimed is:

1. A method of measuring the quality of a coating on the inside of a can comprising the steps of:

i. attaching at least one electric terminal to a can having an inside coating;

ii. inserting an elongate electrode into the can;

iii. applying an electrical signal to at least one of the electrode and the electric terminal;

iv. adding an electrolyte to the can with the electrolyte being in surface-to-surface contact with the inside coating; and v. measuring the current flowing between the electrode and the electric terminal and through the electrolyte as the level of the electrolyte is being varied in a controlled manner to indicate the quality of the inside coating of various parts of the can.

2. The method as defined in claim 1 wherein the current flowing between the electrode and the at least one electric terminal is measured as the electrolyte is being added to the can.

3. The method as defined in claim 1 including the step of measuring the capacitance of the can.

4. The method as defined in claim 1 including the step of interpreting the measured current in terms of the dry film weight of the inside coating.

5. The method as defined in claim 1 wherein the current step is performed at different distances from a base of the can to thereby indicate the quality of the inside coating at such different distances.

6. The method as defined in claim 1 wherein the current step is performed at different distances progressively upwardly from a base of the can to thereby indicate the quality of the inside coating at such progressively upward different distances.

7. The method as defined in claim 1 including the step of applying an AC signal to at least one of the electrode and the electric terminal.

8. The method as defined in claim 7 including the step of measuring the phase relationship between the AC voltage signal applied between the electrode and the electric terminal, and the current flowing between the electrode and the electric terminal.

9. The method as defined in claim 8 including the step of measuring the phase relationship between the AC voltage signal and current by comparing the phase of the current flowing between the electrode and the electric terminal with that of a reference source.

10. The method as defined in claim 9 wherein the reference source is a fixed circuit including a resistor and a capacitor in series to which the AC voltage signal is applied.

11. Apparatus for measuring the quality of a coating on an inside of a can comprising:

i. at least one electric terminal adapted to be attached to a can;

ii. an elongate electrode adapted to be inserted into the can;

iii. a power supply for applying an electric signal to at least one of the electrode and the electric terminal;

iv. means for adding electrolyte to the can in surface-to-surface contact with the inside coating and varying the level of electrolyte in the can at a controlled rate; and v. means for measuring the current flowing between the electrode and the electric terminal and through the electrolyte as the level of the electrolyte is being varied to indicate the quality of the inside coating at various parts of the can.

12. The apparatus as defined in claim 11 where said measuring means measures the current at different distances from a base of the can to thereby indicate the quality for the inside coating at such different distances.

13. The apparatus as defined in claim 11 where said measuring means measures the current at different distances progressively upwardly from a base of the can to thereby indicate the quality for the inside coating at such progressively upward different distances.

* * * * *